(12) United States Patent
Sininger et al.

(10) Patent No.: US 6,196,977 B1
(45) Date of Patent: Mar. 6, 2001

(54) METHOD FOR DETECTION ON AUDITORY EVOKED POTENTIALS USING A POINT OPTIMIZED VARIANCE RATIO

(75) Inventors: Yvonne S. Sininger, Fountain Valley, CA (US); Martyn Hyde, King City (CA); Manuel Don, Anaheim, CA (US)

(73) Assignee: House Ear Institute, Los Angeles, CA (US)

( * ) Notice: Subject to any disclaimer, the term of this patent is extended or adjusted under 35 U.S.C. 154(b) by 0 days.

(21) Appl. No.: 09/300,059

(22) Filed: Apr. 26, 1999

(51) Int. Cl.⁷ .................................................. A61B 5/00
(52) U.S. Cl. ........................................... 600/559; 600/545
(58) Field of Search .................................. 600/544, 545, 600/559

(56) References Cited

U.S. PATENT DOCUMENTS

| | | | |
|---|---|---|---|
| 3,901,215 | 8/1975 | John | 128/2.1 B |
| 4,201,224 | 5/1980 | Roy | 600/544 |
| 4,214,591 | 7/1980 | Sato et al. | 128/731 |
| 4,275,744 | 6/1981 | Thornton et al. | 128/731 |
| 4,462,411 | 7/1984 | Rickards | 128/746 |
| 4,493,327 | 1/1985 | Bergelson et al. | 600/544 |
| 4,844,086 | 7/1989 | Duffy | 128/731 |
| 4,913,160 | 4/1990 | John | 128/731 |
| 5,003,986 | 4/1991 | Finitzo et al. | 128/731 |
| 5,230,344 | 7/1993 | Ozdamar et al. | 600/544 |
| 5,601,091 | 2/1997 | Dolphin | 600/559 |
| 5,697,379 | 12/1997 | Neely et al. | 128/731 |

OTHER PUBLICATIONS

Aoyagi, M. and Harada, J., "Application of Fast Fourier Transform to Auditory Evoked Brainstem Response", *Med. Inform.* (1988), vol. 13, No. 3, pp. 211–220.

Boston, J.R., Denault, L.G., Egol, A.B. and Snyder, J.V. "Objective Response Detection for Sensory Evoked Potentials", *IEEE Frontiers of Engineering and Computing in Health Care*, pp. 220–224.

Dobie, R.A. & Wilson, M.J., "Short–Latency Auditory Responses Obtained by Cross Correlation", *J. Acoust. Soc. Am.*, 76 (5), Nov. 1984, pp. 1411–1421.

Don, M., Elberling, C., and Waring, M., "Objective Detection of Averaged Auditory Brainstem Responses", *Scand. Audiol.* 13 (1984), pp. 219–228.

Elberling, C., and Don, M., "Quality Estimation of Averaged Auditory Brainstem Responses", *Scand. Audiol.* 13 (1984), pp. 187–197.

Friedman, J., Zapulla, R., Bergelson, M., Greenblatt, E., Malls, L., Morrell, F., and Hoeppner, T., "Application of Phase Spectral Analysis of Brainstem Auditory Evoked Potential Detection in Normal Subjects and Patients with Posterior Fossa Tumors", *Audiology* 23 (1984), pp. 99–113.

Herrmann, B.S., Thornton, A.R., Joseph, J.M., "Automated Infant Hearing Screening Using the ABR: Development and Validation", *Amer. J. Audio*, 4, pp. 6–14.

Mason, S.M., "Automated System for Screen Hearing Using the Auditory Brainstem Response", *Brit J. Audiol.*, 22 (1988), pp. 211–213.

(List continued on next page.)

Primary Examiner—Cary O'Connor
Assistant Examiner—Charles Marmor, II
(74) Attorney, Agent, or Firm—Blakely, Sokoloff, Taylor & Zafman LLP

(57) ABSTRACT

A method for determining the statistical probability that an auditory brainstem response (ABR) to an acoustic stimulus is present in a human test subject. The method employs an algorithm that provides a continuously evolving estimate of the probability of ABR presence as acquired data accumulates. The algorithm employs a radical modification of a conventional $F_{SP}$ approach.

10 Claims, 7 Drawing Sheets

OTHER PUBLICATIONS

Moser, J.M., and Aunon, J.I., "Classification and Detection of Single Evoked Brain Potentials Using Time–Frequency Amplitude Features", *IEEE Trans Biomed Eng.*, MBE–33, (1986), pp. 1096,1106.

Özdamar, Ö., Delgado, R.E., Eilers, R.E., and Widen, J.E., "Computer Methods for On–Line Hearing Testing with Auditory Brain Stem Responses", *Ear Hear*, vol. 11, No. 6 (1990), pp. 417–429.

Valdes–Sosa, M.J., Bobes, J.A., Perez–Abalo, M.C., Perera, M., Carballo, J.A., and Valdes–Sosa, P., "Comparison of Auditory–Evoked Potential Methods Using Signal Detection Theory", *Audiology*, vol. 26, 1987, pp. 166–178.

Wicke, J.D., Goff, W.R., Wallace, J.D., and Allison, T., "On–Line Statistical Detection of Average Evoked Potentials: Application to Evoked Response Audiometry (ERA)", *Electroenceph Clin Neurophysiol*, vol. 44 (1978) pp. 328–343.

Wilson, J.J. and Dobie, R.A., "Human Short–Latency Auditory Responses Obtained by Cross–Correlation", *Electroenceph Clin Neurophysiol*, vol. 66 (1987) pp. 529–538.

\* All variances and ratios are accumulative, recalculated after each block of sweeps.

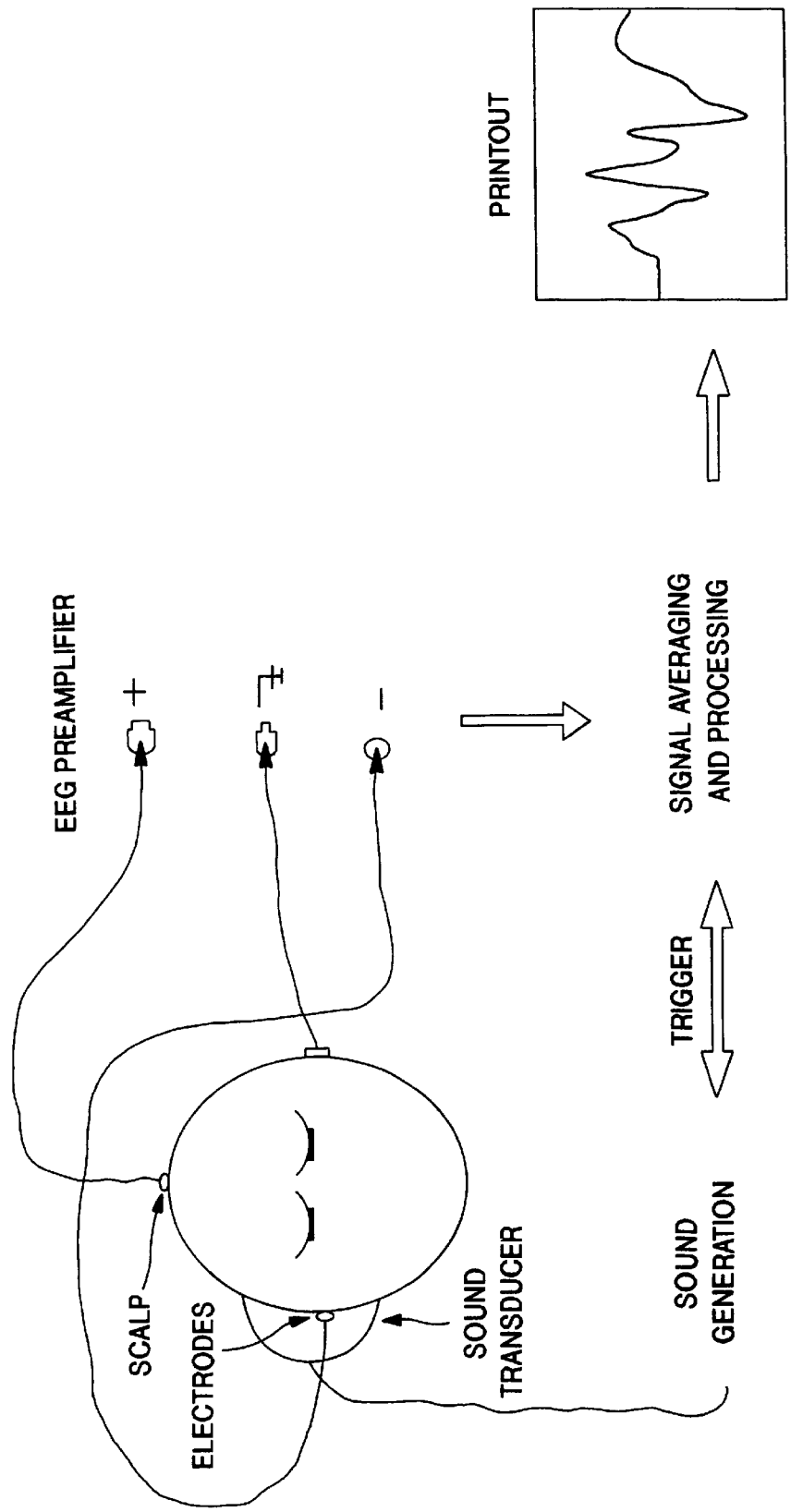

US 6,196,977 B1

METHOD FOR DETECTION ON AUDITORY EVOKED POTENTIALS USING A POINT OPTIMIZED VARIANCE RATIO

BACKGROUND OF THE INVENTION

1. Field of the Invention

The present invention relates generally to the field of assessing hearing capacity in humans. More particularly, the invention is a method for quantifying the probability that an auditory brainstem response (ABR) is present in an electrophysiologic recording from a human infant.

2. Background of the Invention

The ABR is a waveform of fluctuating electrical potential over time, which may occur in response to a brief, transient acoustic stimulus such as a click. The ABR originates in the neurons of the auditory nerve and its higher connections in the brain stem. When recorded from electrodes on the scalp or neck, it is less than one microvolt in size, and is obscured by much larger ongoing random potentials that arise elsewhere in the brain and the musculature of the head and neck. Computer summation or averaging of the responses to several thousand stimuli presented at rates typically in the range of 20–50 per second is required to enhance the ABR "signal" relative to the background electrical "noise", and to render it visually detectable in the summed or averaged response.

The presence or absence of an ABR for a specific type and intensity of stimulus can be used as a proxy for overt behavioral response, indicating whether or not the stimulus was audible. This is the basis for an electrophysiologic hearing screening test, of particular value in subjects such as infants who are unable to give reliable, behavioral responses to sound.

In the newborn population, it is widely acknowledged that it is important to detect and manage hearing loss as early as possible, and preferably in the first six months, to facilitate development of speech, language and cognitive skills. In 1993, the National Institute on Deafness and Other Communication Disorders sponsored a Consensus Conference on Early Identification of Hearing Impairment in Infants and Young Children. That conference recommended screening for identification of hearing impairment in the newborn period for all infants regardless of the presence or absence of risk factors for hearing loss, that is, universal infant hearing screening. These recommendations were endorsed and reiterated soon after by the American Academy of Audiology and the Joint Committee on Infant Hearing, 1984. Many states have recently implemented, or are in the process of implementing, such screening programs. This widespread endorsement of mass hearing screening of neonates and infants has created a challenge for scientists and clinicians to have fast and accurate tools ready for evaluating potential hearing loss in infants.

ABR testing is well established as a core part of most screening protocols. The clinical utility of ABR-based hearing screening tests depends critically on the accuracy of the ABR detection decisions. Such decisions are intrinsically prone to error, because they involve the detection of a signal in random noise that may obscure a genuine signal or masquerade as a signal when none is present. False-positive ABR detection leads to a false-negative screening test: the hearing-impaired child passes the screening test and receives no intervention. Other manifestations of disorder may be ignored, given that the test was passed, so the screening does active harm. False-negative ABR detection tests cause false-positive screening tests; this precipitates needless follow-up diagnostic assessment costs, as well as indirect costs of mislabeling a normal child.

A distinction must be drawn between detection tests that are empirical and those that are analytic. Empirical tests are based upon experimental studies of the distributions of a given test statistic when response is thought to be present or absent. Usually the determination of response presence or absence is based on expert subjective assessment of the average records obtained in a set of subjects. There are two major difficulties with this approach. First, the expert judgments may be wrong, which clearly confounds the assessment of the accuracy of the test statistic. Second, there is no proof that the results observed in one set of subjects will necessarily apply to a different set of subjects or to a situation in which any feature of the data recording or analysis is changed. This is a failure of generalizability of the empirical validation process.

Analytic methods, in contrast, do not appeal to experimental validation datasets. They are based upon known properties of known statistical distributions relating to the chosen test statistic. Thus, rather than relying on empirical experimental data, analytic methods capitalize upon the vast body of statistical distribution theory and statistical tables of distributions. It is necessary to show that real data satisfy certain assumptions that are required for certain distributions to pertain, but these assumptions may be weak, easily satisfied, and easily proven to hold. Such methods are both highly quantitative, yielding known and specifiable rates of decision error, and are also highly generalizible across datasets and measurement conditions.

A crucial characteristic of a good statistical response detection test is that it has the highest possible statistical power. Power is the probability that the test will correctly detect a response that is genuinely present. Less than optimal test power is very disadvantageous in practical terms. A loss of power translates directly to longer test time than necessary to reach the statistical criterion for response detection. This is a major practical disadvantage because some babies yield satisfactory measurement conditions for only brief periods of time, they may be untestable due to test inefficiency. Also testable babies will take longer to test than necessary which increases costs and decreases throughput. This factor will be especially crucial in light of the implementation of universal newborn hearing evaluation protocols now mandated in many states. Third, the use of a test that is less powerful than necessary will result in larger rates of detection decision error than would be possible with a more powerful test.

PRIOR ART DETECTION SYSTEMS

Current approaches to automated detection of ABRs include techniques that evaluate the time-domain waveform and those that assess spectral characteristics (frequency domain). Automated detection of neonatal click-evoked ABR to low-level stimuli for mass screenings have primarily involved analysis in the time domain, although one known system includes both time and frequency domain analysis. At present, four systems have been used or sold as "automated infant ABR screening" devices. By that we refer to those devices in which decisions regarding ABR presence or absence or test "Pass" or "Fail" (sometimes called "Refer") is made by the system itself (not by the examiner) based on some predetermined criteria that are discussed below.

The general approach of the detection algorithm employed by the most commonly used system for automated ABR detection in infants appears to be as follows: A set of sample points are weighted according to their relative magnitude in the standard infant ABR waveform. It is not clear how the position or number of the data points are selected. The polarities of the amplitude of each point in a standard or template are compared with those observed at the corresponding latency in each sweep during averaging. Each time a sweep is sampled, the correspondence of polarity between the data and the template at each of the selected time points yields a count of +1. After every 500 sweeps, the template points are shifted in increments of 0.25 ms over a 3 ms range to locate the position of maximum polarity correspondence. Presumably, this is done using an accumulated average of some kind, but this is not clear. Each sample in each sweep constitutes a trial and running counts of the numbers of polarity matches and trials are accumulated. Because the probability of a polarity match for each point is 0.5 if the response is absent, a quantitative hypothesis test can be constructed based on a binomial model. This technique appears to be a combination of template cross-correlation with a multi-point amplitude-based detection criterion after a one-bit conversion.

The detection algorithm used in this system is statistically based but is far from analytic. Specific disadvantages are as follows:

Lack of validity: The algorithm effectively counts the number of times the polarity of the recorded activity matches the expected polarity of an ABR template waveform. Several points are tested per sweep and the number of polarity coincidences is also summed over many sweeps.

Because the successive data points within each sweep are not statistically independent, the sampling distribution of the number of coincidences will not have the binomial distribution that is assumed. This means that the actual error rates of the test are not represented accurately in statistical tables. Therefore, the method is substantially empirical. Actual error rates may only be determined by experiment with quantitivity and generalizability limitations noted earlier.

Power Sub-optimality: This detection algorithm counts correspondence events between observed and expected polarity of activity at specific times. The actual amplitude of the observed signal is not fully utilized, only the polarity. An analogy can be drawn to the use of the Ordinary Sign Test instead of the Student t-test to examine the hypothesis that the true mean of a sample of n observations is zero. The sign test uses only the polarity of the data, whereas the t-test, which is the most powerful test possible under the assumption of normal error distributions, uses all of the amplitude information. The asymptotic relative efficiency of the sign test is 2/pi, or 64%. This implies that any sign-based detection method will sustain a substantial loss of power.

Another commercially available instrument for ABR hearing screening includes automatic detection that is based on the following algorithm: For any particular stimulus level, the system acquires two ABRs with a fixed stimulus level. The averages are stopped if the estimated signal-to-noise ratio exceeds one or after 1,024 sweeps. If both averages have SNR>1, the response is deemed present. If not, a cross correlation analysis is performed. The latency region of 5 to 12.5 ms post-stimulus is sectioned into seven overlapping 'windows', each of 2 ms duration. For each window position, a Pearson correlation coefficient of the data values in the two averages for each and every successive time point in the given window is calculated. The test variable is the maximum absolute value among the seven correlations covering all window positions. If the test variable exceeds 0.9, the ABR is deemed to be present. This approach to automatic detection is an adaptation of a simple, correlation-based detection method first reported for the ABR by Weber, B. A and Fletcher, G. L., 1980 A Computerized Scoring Procedure for Auditory Brainstem Response Audiometry. *Ear and Hearing*, 1, 233–236. (1980).

The detection algorithm of this device is highly empirical. The primary detection statistic is a cross correlation coefficient between two independent averages using the region of anticipated response. The test statistic is the absolute maximum of the observed correlations. Because of the extensive correlation (autocorrelation) between successive data values in each of the averages, the statistical distribution of the test statistic is unknown, and detection error rates cannot be derived from statistical tables. The critical values for the test statistic, and the error rates, can only be estimated by experiment. Indeed, they were selected using empirical data with expert subjective judgment as the gold standard for response presence or absence. The serious limitations of this method were described earlier.

Details of response detection i n a third prior art system are proprietary, although the manufacturer has released a non-detailed description of the decision-making system. Briefly, the system evaluates three aspects of the infant ABR in the decision process. First, the system determines presence or absence of an ABR in a record by evaluating (a) the presence of a predetermined spectral component of the response, using a multivariate analysis simultaneously assessing both real and imaginary components of a specified Fourier component and (b) an $F_{SP}$-like signal to noise estimate. If those criteria are met, the waveform morphology is checked with a type of template match that evaluates certain features of the waveform (peak number and placement). It appears that all three aspects of response detection algorithm must be satisfied for an infant to receive a "pass" from this system.

Limited information is available about this proprietary detection algorithm. It is based on a combinatorial approach using four types of measure: template (waveshape) and non-template features in both the time and frequency domains. The frequency domain algorithm involves examining the distribution of sine and cosine parts of several harmonics of the Fourier spectrum of the recorded activity, and a comparison with the expected values for both noise and ABR signals. This is combined in an unknown manner with a "modification of the so-called $F_{SP}$ technique". The detection stage is followed by a verification stage that examines the extent to which the detected and estimated waveform matches expected waveshape characteristics.

The performance of this approach is not known and not derivable from statistical distribution theory. The multi-component nature of the method virtually guarantees that it is not of analytic strength, but that it will be empirical. An alleged advantage is its exploitation of both time-domain and frequency-domain features. This is highly questionable, because the time-history and Fourier spectrum of any activity are linear transformations of each other and contain identical underlying information.

$F_{SP}$

A fourth prior art technique that has been applied to infant ABR detection for screening is the $F_{SP}$. This technique is described in Elberling, C. & Don, M. (1984). Quality Estimation of Averaged Auditory Brainstem Responses. *Scand Audiol*, 13, 187–197 and Don, M., Elberling, C. & Waring, M. (1984). Objective Detection of Averaged Auditory Brainstem Responses. *Scand.Audiol.* 13, 219–228. This technique is not applied commercially for specific use in infant screening but is available on some commercial evoked potential systems for general use (Neuroscan and Nicolet "Spirit") and was applied to automated newborn hearing screening by the first named inventor of the present invention in a multi-center study funded by the National Institute on Deafness and Other Communication Disorders. $F_{SP}$ involves calculation of a variance ratio (hence the F) the numerator of which is essentially the sample variance of the average and the denominator of which is the variance of the set of data values at a fixed single point (hence the "SP") in the time window across a group of sweeps.

$F_{SP}$ is used to estimate the "quality" or the signal-to-noise ratio of an auditory evoked potential. Calculation of $F_{SP}$ is based on the fact that any ABR recording is background noise (random brain and muscle activity not related to the auditory signal) and, if the signal is audible to the subject, each recording also contains neural activity from the auditory system that is systematic in scalp recorded morphology and time-locked to the onset of the eliciting auditory signal. For any given single, digitized time point in the averaged ABR waveform, the neural contribution to the amplitude measured at that point is constant from sweep to sweep whereas the noise contribution to amplitude should be random. Consequently, the neural response will contribute nothing to the variance of the amplitude at any single point and the sweep to sweep variance of a single point in the analysis window can be used as an accurate estimator of the variance of the background noise in the recording. This is referred to as VAR(sp).

Calculation of $F_{SP}$ is illustrated in FIG. 1. The magnitude of the averaged response can be characterized by the point to point variance of the digitized amplitude measures for a specified window of the average. In the standard $F_{SP}$ calculation, each point across a specified time window is used in a standard variance calculation referred to as VAR (s). This value is comprised of the energy of the ABR (if present) as well as the energy of the averaged noise. Every 256 sweeps the averaging process is halted momentarily and VAR(s) and VAR(sp) and the ratio of the two ($F_{SP}$) is calculated. The numerator or VAR(s) includes signal and noise and the denominator or VAR(sp) estimates noise. When no signal (ABR) is present the expected value of the ratio is close to 1. The ratio of variances has the known statistical F distribution, indexed by a parameter known as the degrees of freedom (dof). Consequently, when the degrees of freedom are known, the probability of false positive detection for any Fsp value associated with an evoked potential recording can be determined by look up on an F table.

In a standard paradigm, $F_{SP}$ values are updated after each 256 sweeps. As the averaging process reduces background noise, the $F_{SP}$ value associated with a recording containing a true ABR, will grow. A priori rules can be established for halting of the averaging process based on a comparison of achieved and desired probability of true response detection. For example, in the article cited above, Elberling and Don, used a conservative estimation of degrees of freedom and determined that $F_{SP}$ of 3.1 would correspond to true-positive detection confidence of 99%. In that case, the $F_{SP}$ value was used as the stopping criterion for the averaging process, indicating that the desired signal to noise ratio had been achieved. Because any given recording or subject will vary dramatically in the level of the background noise and the amplitude of the evoked potential, using a target $F_{SP}$ as a stopping rule optimizes the use of averaging time, averaging shorter periods of time in good SNR and longer in poor SNR conditions.

The disadvantages of the $F_{SP}$ technique include:

Excessive window length: The standard response analysis window has length 1000/HPF ms where HPF is the high-pass cutoff frequency of the recording amplifier. For a typical case of HPF of 100 Hz, the length is 10 ms. This is generally greater than the length of the region of significant response amplitude. Thus, time regions that contribute little or nothing to the numerator variance estimate are included. This reduces the expected value of the numerator, resulting in a less sensitive test (a test with lower statistical power) than if the window were delimited to regions of substantial response amplitude.

Sub-optimal test points: Even given a response-focused window, some time points within the window contribute more to the response variance than do others. In general, there will exist some subset of all the points in the window that develops maximum variance for a given response waveform, and there will be many other subsets that develop variance substantially greater than the variance of the entire window. It follows that even for a focused window, to select all points in the window as is done in the standard $F_{SP}$ is sub-optimal with respect to statistical power. Both of these disadvantages result in a detection test that is less powerful than necessary.

Conventional $F_{SP}$ can be classed as semi-empirical or semi-analytic. The approach is vastly more quantitative and reproducible than is subjective judgment of response presence or absence. The limitation arises from the fact that the statistical degrees of freedom in the numerator variance estimate are known only approximately. This is due to the fact that the effective degrees of freedom in a time series that has correlation between successive data points, as is the case for ABR data, are not equal to the number of data points used in calculating the variance estimate. For example, a time window containing 100 data points is normally assumed to have 99 degrees of freedom, but may actually only have 10. This means that the distribution of the sample variance of such a set of points will follow chi-square with 10 dof, not chi-square with 99 dof. The distribution of the $F_{SP}$ statistic will change accordingly. Experimental studies have shown that the effective dof in, say, a 10 ms window of ABR data vary slightly across subjects and measurement conditions. Since the dof in a individual subject are not known exactly, but rather, only approximately, the Type I error rate (alpha, the significance level of the response detection test) will be only approximately correct.

Thus a great strength of $F_{SP}$ is that the F-distribution is valid. The qualification is that the decision error rates are not known exactly, only approximately.

SUMMARY OF THE INVENTION

The subject invention provides a method for determining the statistical probability that an ABR to an acoustic stimulus is present in a test subject. This allows the technician to make detection decisions that are valid, consistent and efficient, and which have known and specifiable rates of error. These features offer substantial advantages over current methods, and are especially important in the design of effective and cost-efficient large-scale public health screening programs for infants.

The invention employs a computational algorithm that provides a continuously evolving estimate of the probability of ABR presence as acquired data accumulates. It may be used to determine response probability and to govern when to stop the data acquisition. The algorithm offers substantial improvements over the best available semi-analytic method, namely $F_{SP}$. In particular, the algorithm employed by the present invention improves the power and efficiency of response detection and improves the degree to which the Type I error rate (alpha) and the power can be specified and controlled.

The algorithm, called the Point-Optimized Variance Ratio (POVR), employs a radical modification of the conventional $F_{SP}$ approach. New features are:

i. Specification of a quantitative strategy for optimizing point selection, based on conditional variance of ABR elements and noncentrality of the test statistic.

ii. Incorporation of three critical elements: target waveshape specification, intersubject variation of waveshape position and the autocorrelation structure of the electrophysiologic noise.

iii. Substantial increase in test power and efficiency.

iv. Much reduced reliance on empirical degrees of freedom estimates.

v. Increased accuracy and control of error probabilities.

vi. Reduced test time.

BRIEF DESCRIPTION OF THE DRAWINGS

FIG. 5 diagrammatically illustrates the electrophysiologic data recording procedure of the present invention.

DETAILED DESCRIPTION OF THE INVENTION

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail. The invention set for herein may include elements of the well-known methods and devices disclosed herein above.

POINT-OPTIMIZED VARIANCE RATIO TEST

This invention employs a process by which the statistical power of the conventional $F_{SP}$ is increased, yielding a more efficient test. The key concept is to utilize information about the known position (latency) and morphology of a target ABR waveform so as to maximize the statistical power of the detection test. The first stage in the process is to define the target waveform. This is the waveform that contains all the key morphologic features of the ABR in the intended target population (in this instance human neonates and infants) of candidates for ABR-based hearing screening test. It may be defined either from published scientific data or by experiment. The target ABR waveform is highly consistent across infants in number and relative timing of peaks. However, the absolute latency of peaks has a moderate amount of variance across infants. In several large-sample (N=750) tests of wave V latency in neonates, we have found wave V latency to vary between subjects with a standard deviation of 0.5 ms; the standard deviation of the inter-peak intervals is less than half that amount.

Figure 1:
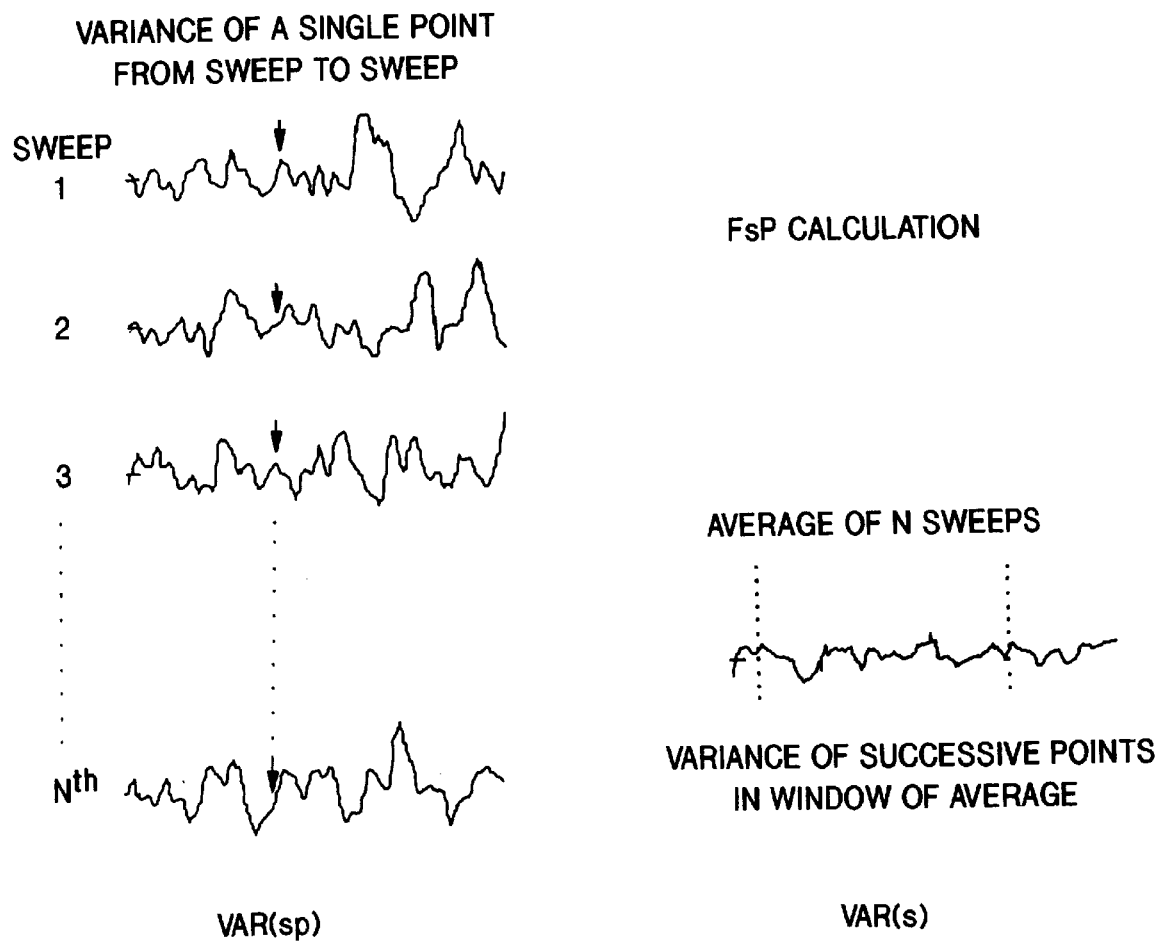
FIG. 1 illustrates prior art calculation of a $F_{SP}$ statistic for ABR waveforms.
Figure 2:
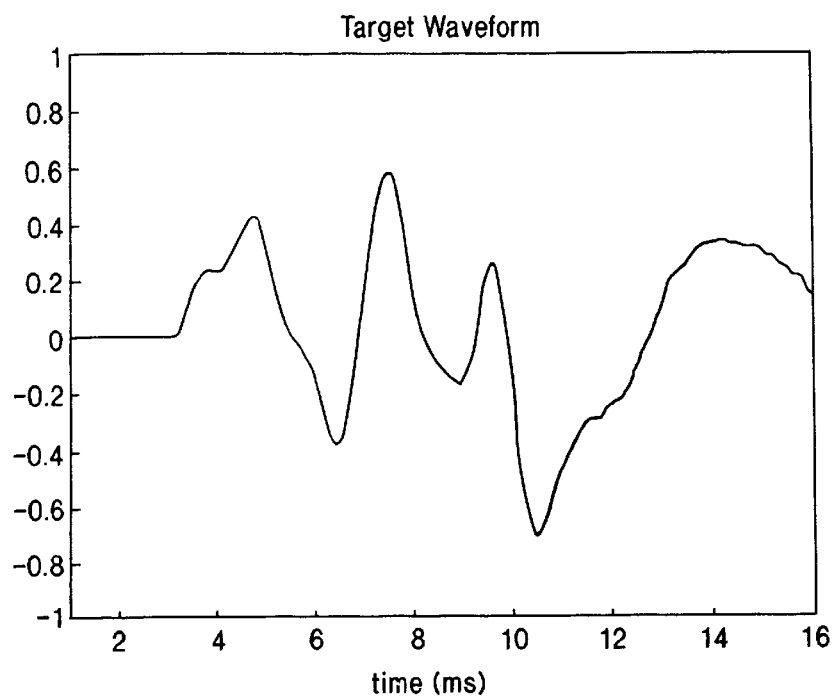
FIG. 2 illustrates an ABR target waveform.

FIG. 2 illustrates a target waveform of a neonatal ABR. Recordings were obtained from ten healthy neonates whose chronological age (gestation plus time since birth) was greater than 39 weeks and whose birthweight ranged from 1850 to 3200 grams. All infants evaluated were assessed by standard techniques (ABR and otoacoustic emission screening) and found to have normal hearing status. Electrophysiologic data was acquired via scalp electrodes attached to the vertex and mastoid ipsilateral to the stimulated ear. Ten thousand triggered sweeps of EEG, in response to 30 dB nHL click stimuli, were stored off-line for each infant. This high number of sweeps was used to insure adequate reduction of background noise during averaging. In addition, all sweeps with excessive EEG amplitude, thought to be myogenic artifact, were rejected before averaging. Averaged waveforms of 20 ms duration were inspected for morphology and the latency of the largest peak, wave V, was determined. Each average was scaled to unit peak amplitude for wave V and then aligned with respect to the peak latency of wave V. A grand-average ABR was created and wave V latency was set to the mean of the latencies of the original 10 averages. The waveform was cropped to 1–16 ms and zeroed from 1–3 ms.

Although the ABR has standard features such as number and prominence of peaks, peak latencies and amplitudes, waveform morphology is dramatically influenced by specific stimulus and recording characteristics of each system, especially EEG filtering characteristics. Target waveforms must be derived from data acquired on the target population (for example infants) from the recording system and with the recording characteristics on which the algorithms will be applied. In other words, the point selection process must be customized for each type (model) of recording system.

The second stage of the process is to select a highly specific set of points from the entire window that includes non-zero values of the target ABR waveform. The point selection process is designed to maximize the statistical power of the detection test. The process operates on the target ABR waveform so as to yield a subset of all the points in the window containing non-zero response.

Figure 3:
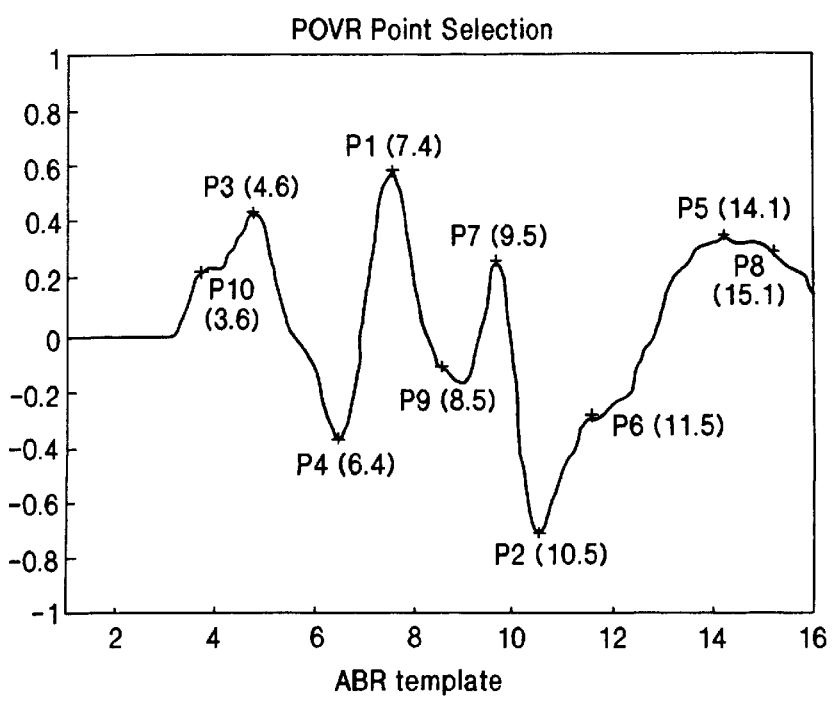
FIG. 3 illustrates waveform point selection used in the invention.

With reference to FIG. 3, candidate point sets are selected as follows:

a) Select maximum and minimum values. These are the first two points.

b) Compute the maximum 3-point signal variance for all possible positions of the $3^{rd}$ point, with the constraint that the $3^{rd}$ point cannot be closer than 1.0 ms to any previously chosen point.

c) Select the $3$rd point position yielding the maximum conditional variance under the proximity constraint.

d) Iterate steps b and c above for the $4^{th}$ through kth additional points stopping when the maximum conditional variance is some specified fraction of the largest (2-point) variance.

In our studies the fraction was ⅕ and 10 points were selected with latencies as shown in parentheses.

For the point selection strategy applied here, a constraint that a minimum distance of 1 ms between two points has been employed. This avoids large absolute values of autocorrelation between successive data points in the ABR noise. The envelope of the ABR noise autocorrelation function tends toward zero at intervals of 1 ms or greater. Consequently, the selected points are assumed to be approximately statistically independent. Under these conditions, the dof of any subset of the points of size m will be m−1.

Any point set will perform best when optimally positioned for the response location in the individual subject. In our studies, the point selection corresponding to the prominent and well-defined peak wave V in the target waveform was positioned at the observed maxima in the wave V latency region for each of several sets of representative ABR data with the desired stimulus conditions for screening. Ideally, this should be done for a novel set of data, distinct from that used to develop the target waveform.

Next, for each and every candidate point set of size 2 through 10 using data from each subject in the normative group, cumulative values of the modified $F_{SP}$ are computed for number of sweeps (n) typically ranging from 1 to 5000. For each successive value of n, the probability of obtaining an F value greater than or equal to the observed value is obtained from the F-table lookup. In general, this probability declines systematically as n increases and the values for each n define what is here called the "probability function." A convenient representation is a plot of $-\log_{10} p$ where p is the probability. This is actually the likelihood of rejecting the null hypothesis of ABR absence. For an alpha of 0.01, the value of $-\log_{10}$ is 2. p When the probability curve meets or exceeds 2, the ABR is deemed to be present (the null hypothesis is rejected).

The advantage of using probability curves to quantify the strength of any given point selection is that it immediately makes clear the number of sweeps needed to achieve the criterion value (alpha). This is the most relevant, practical impact of improvement in test power. The reduction in n relative to that needed using the baseline $F_{SP}$ with all points selected is monotonic with the test power increase, and translates immediately into reduced data acquisition time in the clinical application. In general, the optimal point selection may vary from subject to subject, but there are systematic trends in average performance over the subject group.

A suitable method of determining the best point selection is to rank the number of sweeps required to reach criterion, for all candidate point sets, and then select the set yielding the lowest average rank over the group of subjects. The point-selection efficiency relative to the baseline $F_{SP}$ can be expressed as the ratio of the n needed for baseline divided by the n needed for the point set. A halving of the required n equals a doubling of efficiency or an "efficiency ratio" of 2.

The procedure above yields the best point set on average over the subject group, and quantifies the gain from using that set, under conditions wherein the subject's ABR is positioned in time at or close to the position of the defined ABR waveform. If there is latency shift for any individual subject, the test power will, in general, be reduced and the amount of reduction may change with both the amount of latency shift and the nature of the point set used.

One way of accommodating this effect is to determine the range of observed wave V latencies in the normative subjects, and to modify the dof associated with each point set. This will change the probability curves, and may, as a result, modify the ranking of point set performance. The dof adjustment procedure is as follows: For the no-stimulus ABR noise data, the sample cumulative distribution function of the F statistic for each point set is obtained and fitted to tabulated values for various dof, as described earlier. However, the F statistic is not the maximum value observed for a small number of point set positions spanning the range of possible wave V latencies observed in the stimulation data from normative subjects. Typically about 3 to 5 point set positions may be appropriate. Given the adjusted dof, probability curves can be computed and their characteristics summarized as described above.

It is appropriate to examine both the unadjusted and adjusted performance data. The best performance analysis is the primary guide for point selection. The amount of latency variation is dependent on the precise nature of the target population and the test protocol. Adjustments of the point selection based on any changes in performance with modified dof should be considered as a correction process tailored to specific screening circumstances.

$F_{SP}$ is fundamentally a variance ratio test. The ratio may be denoted as Var(num)Var(denom). The numerator variance Var(num) is conventionally calculated as the sample variance of the k contiguous data points observed in some time window of the average of N sweeps (epochs of electrophysiologic activity, each epoch being time-locked to a stimulus event). Var(denom) is derived from the sample variance of a single data matrix column, that is, the sample variance of the set of N source data points that occur at a given, selected time interval after the start of each and every sweep. The raw sample variance is scaled down by a factor N, to estimate the variance of a mean of N sweeps, as dictated by standard distribution theory.

Var(num) has some number of degrees of freedom (dof) that is determined empirically from normative studies. It does not have k-1 dof as might be expected, because the successive points in the digitized recording may be strongly correlated (auto-correlated). Var(denom) has N-1 dof, because the points are not contiguous, each one coming from a separate sweep. Thus, the points are taken at time interval large enough that the auto-correlation function has declined to virtually zero.

Under the null hypothesis of no ABR, the two variances estimate a common underlying variance. Therefore, their ratio is distributed as F with m and N-1 dof. In the absence of ABR, the expected value of the sampling distribution of the ratio tend to unity as the denominator dof increase. When the ABR is present (non-zero), the denominator variance estimate is unchanged because the ABR is deemed to be constant over sweeps at any given point in time in each sweep. In contrast, the sample variance of the numerator is increased by an additive component v, where v is the mean square magnitude of the ABR. Under these conditions, the null hypothesis is false and the sampling distribution of the ratio is noncentral F, with dof m and N-1. The factor v displaces the distribution positively, compared to central (regular) F; the quantity v/o, where o is the population variance estimated by Var(denom), is called the noncentrality parameter of the non-central F distribution. Because o is assumed constant, the noncentrality parameter is proportional to the mean square ABR magnitude.

The occurrence of a large observed value of $F_{SP}$ leads to rejection of the null hypothesis, that is, to the decision that an ABR is present. The critical value for the decision is derived from tables of central F, usually being the value of F such that the probability of observed F exceeding the critical value is 0.01 (alpha, Type I error probability) under the null hypothesis. When the null hypothesis is false, this probability is the test power, and tends to unity for very large values of the noncentrality parameter. The power is a monotonic increasing function of that parameter.

In conventional $F_{SP}$, the mean square ABR value is a component of the numerator variance Var(num), and is computed using each and every data point in some time window thought to cover the response. Because the ABR is at or close to zero at some time points (being an oscillatory waveform), it follows that the mean square value is less than it would be if such points were not included. That is, it is possible to select a subset of the full set of k points, such that the ABR mean square will be larger than that in the conventional $F_{SP}$. Other things being equal, increasing the mean square ABR increases the non-centrality, and therefore the power of the F-test of the null hypothesis.

A distinguishing characteristic of the invention is that, of all the possible sets of test points, the one selected is that which maximizes the test power for a given target waveform. Equivalently, the best point selection is that which maximizes the non-centrality parameter of the distribution of the test statistic, when the target response is present. This property of POVR clearly distinguishes it from the conventional $F_{SP}$ and, even more strongly, from all non-analytic test procedures. Because the quantity v is monotonic with power and non-centrality, it is sufficient to maximize v. Many methods for maximizing v are possible. The method used in development of the present invention was to begin with the two points on the target waveform that maximize the 2-point variance. These will automatically be the target waveform minimum and maximum. Next, given the first two points, the point selection algorithm explores all points to find the point that maximizes the conditional variance. Because of the highly autocorrelated nature of the ABR noise data, it is known that selection of test points that are very proximal will be inefficient; because of the high positive correlation between proximal points in the noise, the effective dof in the resulting statistic will be small. For a given number of test points, the larger the dof the better, so the power maximization comprises a joint optimization of ABR variance and dof. The latter facet of the strategy is governed by the autocorrelation function (auto correlation coefficient for all possible intervals between two points) of the ABR noise. Based on autocorrelation data of real baby noise recordings, the constraint was imposed that two selected points could not be closer together in time than 1 ms.

Another feature of the present invention is allowance for the fact that, while ABR morphology is generally similar across test subjects, the overall ABR waveform may vary in its post-stimulus time position (latency). If the power-optimizing point selection is addressing an ABR that is positioned exactly at the median position used to derive the target waveform, its power will truly be optimal. Latency shift will in general cause power loss and it is to be expected that the more focused the selected point set is in time, the greater the power loss will be. One approach to this problem is to apply the test to the maximum value of the test statistic, the latter being computed for several time positions that both span the expected domain of possible ABR latencies and take into account the temporal dependency of power on the test point positions relative to the actual ABR. In general, this multi-position method will cause an increase in the Type I error rate, relative to the fixed-position value. It is expected that the power gain by multi-positioning will more than offset the power reduction caused by adjusting the critical value for the F-test so as to correct the Type I error rate.

Figure 4A:
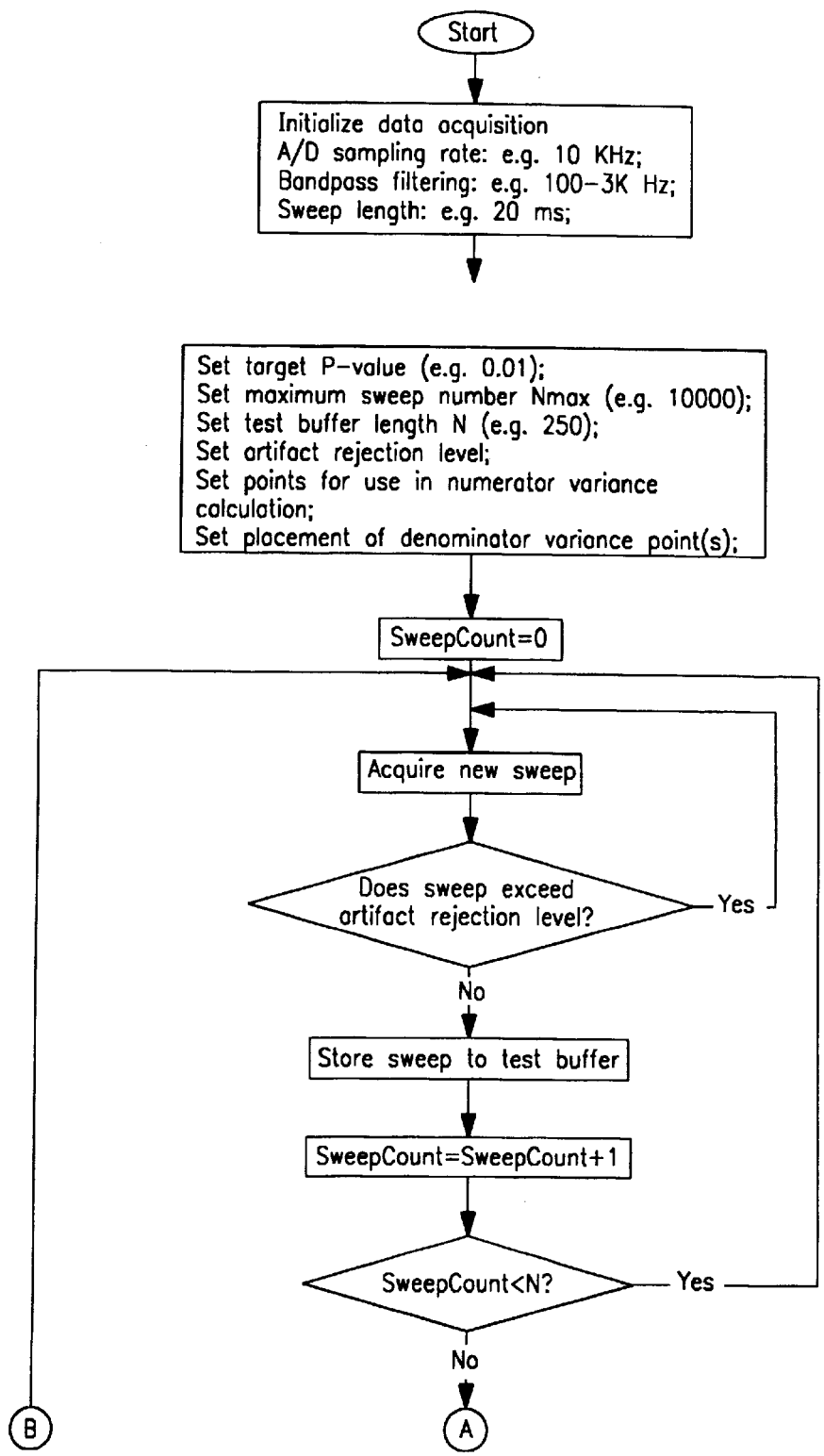
FIG. 4a, 4b is a functional flow diagram of the diagnostic procedure of the invention.
Figure 4B:
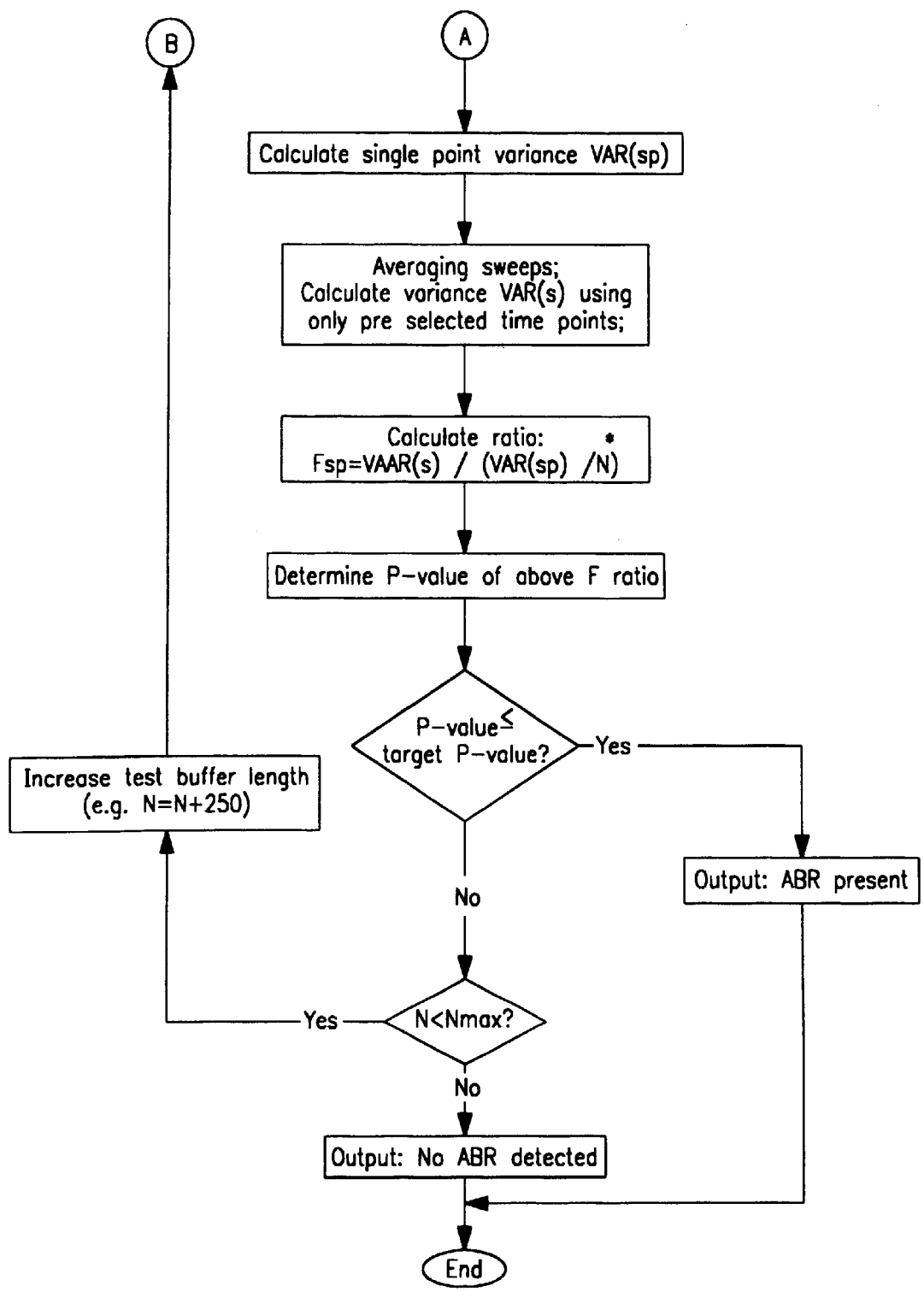

FIG. 4a, 4b is a flowchart of the screening test in accordance with this invention. The procedure begins with routine setting of acquisition parameters for the A/D converter including sampling rate appropriate for ABR and data filtering etc. In the example used, 20 ms of activity is digitized at 10,000 Hz (200 points). At this time the technician also decides the target P-value for the test. For example, a P-value of 0.01 indicates 99% confidence that the ABR detected is an actual response. The maximum number of sweeps is selected, which indicates how long the testing should continue before stopping. The test buffer length is also referred to as the block size. This is the sub-sample of sweeps between each recalculation of the test statistic. Artifact rejection level is a voltage level. Because unwanted activity such as muscle responses, have very large voltage relative to the neural response, any sweep containing very large excursions is not used to avoid excessive contamination of the data.

Choosing the points for the numerator variance calculation is a step that is completed prior to the test and has been described in detail above. The single point placement selection is used for denominator variance calculation. This placement can be at any point or set of points between the points used for the numerator.

The acquisition of each sweep of EEG is accomplished using standard techniques. A schematic of the instrumentation is shown in FIG. 5. EEG activity is acquired by means of scalp-applied electrodes connected by lead wires to a differential preamplifier. The preamplifier subtracts signals recorded from two scalp placements to eliminate like components of the recordings assumed to include noise (activity other than neural evoked potentials). Placement of these electrodes should be carefully chosen to optimize the recording of target waveforms. Signals are amplified and bandpass filtered with filter specifications chosen specifically to enhance the target activity.

EEG activity is sectioned into epochs or sweeps of user-determined duration, for example 10–30 ms. Activity is digitized with a sampling rate appropriate for the spectral content of the signal. A triggering mechanism is used to synchronize the sampling of each sweep and the presentation of appropriate auditory stimuli with a user-selected inter-stimulus interval. The stimulus is generally a 100 $\mu$s square-wave pulse that produces a click when applied to the appropriate transducer. However, other stimuli such as a short-duration ramped tone (tone burst) could also be used.

With reference again to FIG. 4, as each block of sweeps is collected, the calculation of the test statistic takes place. The associated P-value is then determined and compared to the target P-value initially set by the technician. If the target is not reached, the entire process repeats. Recording is halted when response presence or absence is determined in accordance with the target P-value. The device may or may not have a hard-copy printout of response, or may have a more simplified indicator of the response decision such as "pass" or "fail".

EXPERIMENTAL RESULTS

Twelve, healthy newborns were evaluated at the Infant Auditory Research Laboratory of Los Angeles County+ University of Southern California Medical Center, Women's and Children's Hospital. One or both ears were assessed by standard ABR techniques using both 30 dB nHL click stimuli or in no-stimulus conditions. In each condition, 10,000 individual sweeps of 20 ms duration were stored off-line for lab analysis. Data was acquired via a Neuroscan "Synamps" amplifier and Scan acquisition software, data was digitized at 10 k Hz and filtered from 100 to 3000 Hz.

Figure 6:
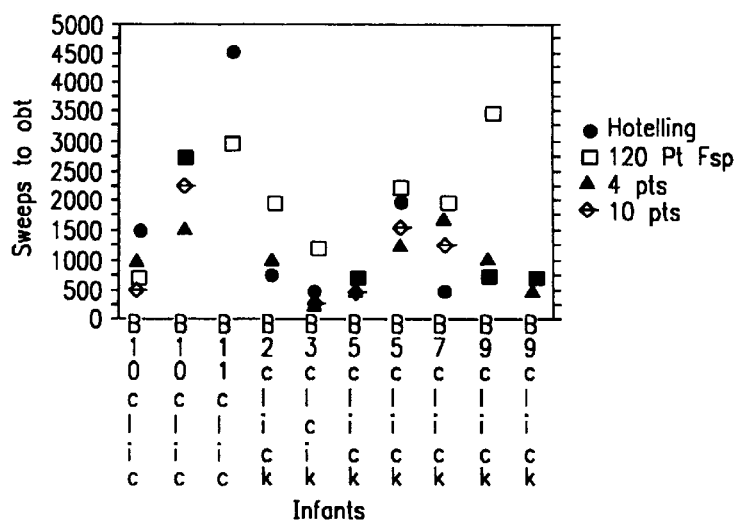
FIG. 6 is a data plot comparing performance of the present invention with prior art $F_{SP}$ and another new type of analysis.
Figure 7:
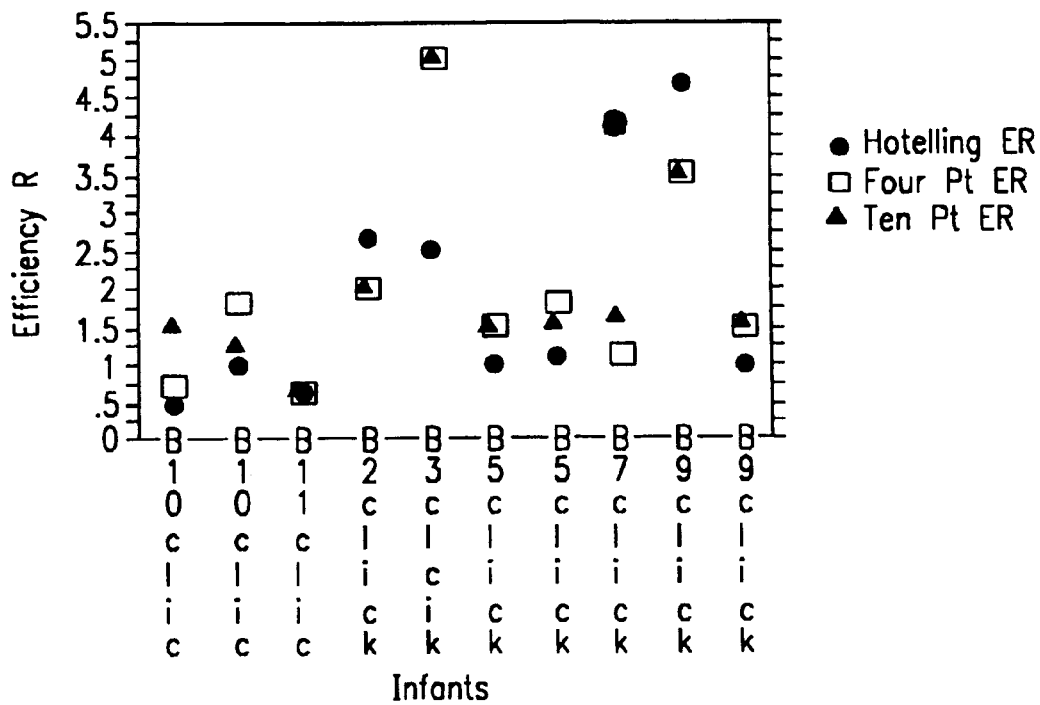
FIG. 7 is a data plot comparing efficiency of the present invention with prior art $F_{SP}$ and another new type of analysis.

Electrophysiologic recordings with click stimuli were analyzed with the present invention (POVR), with another algorithm (Hotelling $T^2$) and with standard $F_{SP}$. Probability curves were constructed for each set of data using standard (120 pt) $F_{SP}$, POVR with 4 and 10-point selections and Hotelling $T^2$. The intersection of $-\log_{10} p=2$ revealed the number of sweeps necessary in each condition to reach alpha of 0.01. Those data are plotted in FIG. 6. A significant reduction in the number of sweeps was found for both the POVR and Hotelling algorithms when compared to standard $F_{SP}$. Efficiency ratios (#sweeps in standard $F_{SP}$ condition/# sweeps in test condition) for 3 tests are shown in a scatterplot on FIG. 7.

The 120-point (standard) $F_{SP}$ can be considered as a baseline against which to evaluate the invention. It should be noted that each set of measurements in a given baby constitutes an element of a random sample of possible observed values of the statistics. Thus, fluctuation in the numbers of sweeps required, and differences from case to case in the relationships between the statistics, are to be expected. Relative to the 120-point $F_{SP}$ baseline, the invention improves the efficiency of measurement in all cases except case B11 clickr. In several cases, the improvement is dramatic (such as for B9clickl). Such a result may well make the difference as to whether any valid screening result at all could be obtained practically in such a case. In general, the gains are expressed by the average values of the efficiency ratios, which are very favorable.

The present invention has been described in the context of a screening process utilizing auditory brainstem response (ABR). Another physiologic measure currently in use for evaluation of hearing status in newborn infants is otoacoustic emissions (OAE). Screening techniques using this measure have been shown to be fast and reasonably accurate in identifying hearing impairment in newborns. As with ABR, OAE is amenable to objective response detection and automation. The detection algorithms described herein could also be applied to OAE with only minor modifications.

It will be recognized that the above described invention may be embodied in other specific forms without departing from the spirit or essential characteristics of the disclosure. Thus, it is understood that the invention is not to be limited by the foregoing illustrative details, but rather is to be defined by the appended claims.

What is claimed is:

1. A method for gathering and analyzing ABR signal data generated in response to auditory stimuli to determine hearing capacity of an individual based on a ratio of the variance of average ABR data at specific time points specified by a target waveform to the variance of data at fixed points in time from single sweeps that will form the average, comprising the steps of:

(a) generating a plurality of auditory stimuli;
   (b) presenting said auditory stimuli to a test subject's ear;
   (c) collecting electrophysiologic signal data from the test subject within a sweep following each of a specified number of said auditory stimuli;
   (d) computing a cumulative variance of data at predetermined points in time across individual sweeps;
   (e) computing a cumulative test subject average waveform from said collected electrophysiologic signal data;
   (f) computing a variance of selected points on said cumulative test subject average waveform;
   (g) computing a variance ratio with the variance computed in (f) as numerator and variance computed in (d) as denominator;
   (h) computing a probability value associated with said ratio;
   (i) continuing steps (a) through (h) adding to the cumulative test subject average waveform and single sweep data if said computed probability value exceeds a predetermined threshold and declaring that the test subject responded to the auditory stimulus if the computed probability value is below said predetermined threshold; and
   (j) terminating steps (a) through (h) and declaring that no response is present if a predetermined number of stimuli have been presented without the computed probability value falling below the predetermined threshold.

2. The method of claim 1 wherein the probability value computed in step (h) is based on standard F tables.

3. The method of claim 1 wherein the selected points in step (f) comprise a subset of points on the target waveform having a non-zero response.

4. The method of claim 3 further comprising the step of selecting said selected points by:

(i) selecting maximum and minimum values on a target waveform as first and second points;
   (ii) computing a maximum n-point signal variance for a plurality of candidate $n^{th}$ points;
   (iii) selecting as an $n^{th}$ point one of the plurality of candidate $n^{th}$ points yielding maximum variance;
   (iv) repeating steps (ii) and (iii) to select additional points until the maximum variance determined in step (iii) is below a predetermined threshold.

5. The method of claim 4 wherein the plurality of candidate n points are constrained to be no closer than a predetermined time value to any of the previously selected n-1 points.

6. A system for gathering and analyzing ABR signal data generated in response to hearing stimuli to determine hearing capacity of an individual based on a ratio of the variance of average ABR data at specific time points specified by a target waveform to the variance of data at fixed points in time from single sweeps that will form the average comprising:

(a) means for generating a plurality of auditory stimuli;
   (b) means for presenting said auditory stimuli to a test subject;
   (c) means for collecting electrophysiologic signal data from the test subject within a time window following each of a specified number of said auditory stimuli;
   (d) means for computing a cumulative variance of data at predetermined points in time across individual sweeps;
   (e) means for computing a cumulative test subject average waveform from said collected electrophysiologic signal data;
   (f) means for computing a variance of selected points on said cumulative test subject average waveform;
   (g) means for computing a variance ratio with the variance computed by (f) as numerator and variance computed by (d) as denominator;
   (h) means for computing a probability value associated with said ratio;
   (i) means for iteratively operating (a) through (h) adding to the cumulative test subject average waveform and single sweep data if said computed probability value exceeds a predetermined threshold and declaring that the test subject responded to the auditory stimulus if the computed probability value is below said predetermined threshold; and
   (j) means for terminating operation of (a) through (h) and declaring that no response is present if a predetermined number of stimuli have been presented without the computed probability value falling below the predetermined threshold.

7. The system of claim 6 wherein the probability value computed by (h) is based on standard F tables.

8. The system of claim 6 wherein the means for computing a variance of selected points computes a variance of a subset of points on the target waveform having a non-zero response.

9. The system of claim 8 further comprising means for selecting said selected points by:

(i) selecting maximum and minimum values on the target waveform as first and second points;

(ii) computing a maximum n-point signal variance for a plurality of candidate $n^{th}$ points;

(iii) selecting as an nth point one of the plurality of candidate $n^{th}$ points yielding maximum variance;

(iv) repeating steps (ii) and (iii) to select additional points until the maximum variance determined in step (iii) is below a predetermined threshold.

10. The system of claim 9 wherein the plurality of candidate $n^{th}$ points are constrained to be no closer than a predetermined time value to any of the previously selected n-1 points.

* * * * *

UNITED STATES PATENT AND TRADEMARK OFFICE
CERTIFICATE OF CORRECTION

PATENT NO.    : 6,196,977 B1
DATED         : March 6, 2001
INVENTOR(S)   : Sininger et al.

Page 1 of 1

It is certified that error appears in the above-identified patent and that said Letters Patent is hereby corrected as shown below:

<u>Title page,</u>
Item [54], delete "ON AUDITORY" and insert -- OF AUDITORY --.

Signed and Sealed this

Sixth Day of August, 2002

*Attest:*

*Attesting Officer*

JAMES E. ROGAN
*Director of the United States Patent and Trademark Office*